US006807323B2

United States Patent
Beom et al.

(10) Patent No.: US 6,807,323 B2
(45) Date of Patent: Oct. 19, 2004

(54) ACTIVE ION-DOPED WAVEGUIDE-PLASMON RESONANCE SENSOR BASED ON UPCONVERSION OF ACTIVE IONS AND IMAGING SYSTEM USING THE SAME

(75) Inventors: Shin Yong Beom, Daejon (KR); Hyeon-Bong Pyo, Daejon (KR); Jiwook Jeong, Daejon (KR); Lee Sang-Kyung, Daejon (KR); Dong Ho Shin, Daejon (KR); Min-Gon Kim, Daejon (KR); Park Seon Hee, Daejon (KR)

(73) Assignee: Electronics and Telecommunications Research Institute (KR)

( * ) Notice: Subject to any disclaimer, the term of this patent is extended or adjusted under 35 U.S.C. 154(b) by 137 days.

(21) Appl. No.: 10/090,305

(22) Filed: Mar. 4, 2002

(65) Prior Publication Data

US 2003/0099422 A1 May 29, 2003

(30) Foreign Application Priority Data

Nov. 23, 2001 (KR) .................................... 2001-0073283

(51) Int. Cl.[7] .............................................. G02B 6/00
(52) U.S. Cl. ........................................ 385/12; 385/141
(58) Field of Search .......................... 385/12, 129–132, 385/141, 142

(56) References Cited

U.S. PATENT DOCUMENTS

| 4,649,280 | A | * | 3/1987 | Holland et al. | .......... 250/483.1 |
| 4,844,613 | A | * | 7/1989 | Batchelder et al. | ......... 356/318 |
| 4,889,427 | A | * | 12/1989 | Van Veen et al. | ........... 356/445 |
| 5,359,681 | A | * | 10/1994 | Jorgenson et al. | ............ 385/12 |
| 5,677,769 | A | * | 10/1997 | Bendett | ...................... 356/440 |
| 5,991,488 | A | * | 11/1999 | Salamon et al. | ............ 385/129 |

* cited by examiner

Primary Examiner—John D. Lee
Assistant Examiner—Sarah Song
(74) Attorney, Agent, or Firm—Blakely Sokoloff Taylor & Zafman

(57) ABSTRACT

An active ion-doped waveguide-plasmon resonance (AID WPR) sensor based on plasmon surface resonance (PSR) and an imaging system using the sensor are provided. An additional dielectric thin film doped with active ions and acting as a waveguide is formed on a metal thin film. The active ions are excited by an incident light beam and fluoresce light of a shorter wavelength than the incident light beam through upconversion coupled to surface plasmon resonance, thereby increasing fluorescence intensity variations with respect to incident light angle variations. The AID WPR sensor and the imaging system can detect a minor refractive index variation of a sample, which could not be measured using an existing SPR sensor, or a trace adsorbed material, with 100 times larger refractive index resolution than the existing SPR sensor.

55 Claims, 15 Drawing Sheets

ACTIVE ION-DOPED WAVEGUIDE-PLASMON RESONANCE SENSOR BASED ON UPCONVERSION OF ACTIVE IONS AND IMAGING SYSTEM USING THE SAME

CROSS-REFERENCE TO RELATED APPLICATIONS

The present application claims priority to Korean Application No. 2001-73283 filed Nov. 23, 2001, the disclosure of which is incorporated herein by reference in its entity.

BACKGROUND OF THE INVENTION

1. Field of the Invention

The present invention relates to a sensor for use in sample analysis and its applications, and more particularly, to a surface plasmon resonance sensor and an imaging system based on the principle of the surface plasmon resonance sensor.

2. Description of the Related Art

Surface plasmon is a quantized oscillation of free electrons that propagates along the surface of a conductor such as a metal thin film. Surface plasmon is excited to cause resonance by an incident light beam entering a metal thin film through a dielectric medium such as a prism at an incident angle greater than a critical angle. This phenomenon is referred to as "surface plasmon resonance" (SPR). The incident angle of an incident light beam that causes resonance is very sensitive to changes in the refractive index of a material closest to the metal thin film. SPR sensors developed based upon the above principle have been widely used for quantification and qualification of a sample or measurement of a sample (thin film) thickness from changes in the refractive index of the sample displaced closest to the metal thin film.

FIG. 1 shows a typical SPR sensor based on the Kretschmann configuration. Referring to FIG. 1, the SPR includes a unit U composed of a dielectric medium 10 and a metal thin film 22 that induces SPR. A half-cylindrical or triangular prism made of transparent glass, such as BK7 and SF10, is often used for the dielectric medium 10. The metal thin film is formed of gold or silver with a thickness of 40–50 nm. The unit U is supported by a rotary plate 50 capable of rotating around a fixed shaft. A sample 23 of interest to be measured for changes in its refractive index within the surface plasmon field is brought into contact with the metal thin film 22 of the unit U.

In FIG. 1, reference numeral 30 denotes a light source fixed to emit an incident light beam 31 toward the metal thin film 22, and reference numeral 40 denotes a photodetector for measuring the intensity of the reflected light from the surface of the metal thin film 22. A monochromatic laser, a monochromic light emitting diode (LED), a white light source of multiple wavelengths, or a multiple-wavelength LED is often used as the light source 30.

SPR occurs when the wave vector of the incident light beam 31 parallel to the surface of the metal thin film 22 is equal to the wave vector of the surface plasmon wave. Thus, the following formula (1) is satisfied:

$$n\sin\theta_{re} = \sqrt{\frac{\varepsilon_1\varepsilon_2}{\varepsilon_1+\varepsilon_2}} \quad (1)$$

where n is the refractive index of the dielectric medium, $\theta_{re}$ is the resonance angle, and $\varepsilon_1$ and $\varepsilon_2$ are the dielectric constants of the metal thin film 22 and the sample 23, respectively.

As is apparent from the formula (1) above, if the resonance angle $\theta_{re}$ is given, the dielectric constant of the sample 23 can be calculated using the formula (1) and thus changes in the refractive index of the sample 23 or with respect to a reference sample can be observed. As a consequence, measurement of the thickness of the sample 23 if it is a thin film, or quantification and qualification of the sample adsorbed onto the metal thin film 22 can be implemented from the changes in the refractive index.

Resonance angle $\theta_{re}$ can be measured using a variety of methods.

First, the fact that the intensity of the reflected light (or reflectance) 39 has a minimal value when the metal thin film 22 is excited to induce SPR by the incident light beam 31 is used. In this method, the intensity of the reflected light (or reflectance) 39 is measured while changing the incident angle $\theta$ of the incident light beam 31, and the resonance angle $\theta_{re}$, the incident angle at which resonance occurs, is read from a plot of the intensity of the reflected light (or reflectance) 39 as a function of the incident angle $\theta$. The intensity of the reflected light (or reflectance) 39 is measured while rotating the rotary plate 50 to vary the incident angle $\theta$, in which a monochromic light source as the light source 30 and a prism with a constant refractive index as the dielectric medium 10 are used.

In a second method, a wavelength where SPR occurs is found by emitting the incident light beam 30 at a fixed incident angle $\theta$ using a white light source of multiple wavelengths as the light source 30. As a result, the resonance angle $\theta_{re}$ and resonance wavelength can be obtained simultaneously.

In a third method, the resonance angle $\theta_{re}$ is measured by emitting a monochromic light from the light source 30 within the range of the incident angle to the center of the dielectric medium 10 and by receiving the light reflected from the surface of the metal thin film 22 with the same range of angles as the incident angle using a multi-channel photodetector, such as a photodiode array (PDA), as the photodetector 40. This method is disclosed in U.S. Pat. Nos. 4,889,427; 5,359,681; and 4,844,613.

The method of measuring the resonance angle $\theta_{re}$ using a monochromatic light as in the first and third methods described above has about 10 times higher sensitivity than the second method using a white light source at a fixed incident angle. For this reason, the first and third methods have been used widely, and products based on the third method are available from Biocore and Texas Instrument.

FIG. 2 shows reflectances as a function of the incident angle of light measured using the SRP sensor of FIG. 1 for samples of different refractive indices. In FIG. 2, (1) is for water, (2) is for a sample with a refractive index difference of $10^{-6}$ from water, and (3) is for a sample with a refractive index difference of $10^{-3}$ from water.

An inset for a portion A in FIG. 2 shows changes in resonance angle with respect to changes in the refractive index of samples. A change in resonance angle ($\Delta\theta$) by about 0.0001° occurs between samples (1) and (2) having a refractive index difference of $10^{-6}$. In measuring the resonance angle by the first and third methods described above, the rotary plate 50 used in the first method to vary the incident angle has an angular resolution limit of about 0.0001° and the photodetector 40 such as a PDA which spatially splits the light reflected within a predetermined range of angles has a resolution limit of about 0.0001°. Thus, it is difficult for the SPR sensor with such a resolution limit to detect a minor change in refractive index less than $10^{-6}$ or equivalent physical quantities, for example, protein adsorbed onto the surface of a metal thin film in an amount of less than several picograms per 1 mm². In addition, adsorption of a material having a molecular weight less than 200 cannot be detected.

In the method of measuring reflectance at a fixed incident angle $\alpha$, a change in reflectance ($\Delta R$) for a refractive index difference of $10^{-6}$ between samples is only 0.03% at $\alpha=65.0304°$. In consideration of the 0.2% resolution of a measuring system commonly used in the field, this method has a lower refractive index resolution than the methods for directly measuring the resonance angle.

To address the limitations of the SPR sensor, a coupled plasmon-waveguide resonance (CPWR) sensor, as shown in FIG. 3, has been developed. In FIG. 3, the same elements as those in FIG. 1 are denoted by the same reference numerals as those in FIG. 1.

Referring to FIG. 3, the CPWR sensor with improved sensitivity is a modification of the SPR sensor of FIG. 1. The CPWR sensor, which is disclosed in U.S. Pat. No. 5,991,488, includes a dielectric thin film 60 between the metal thin film 22 and the sample 23. The dielectric thin film 60 is formed as a single or multiple layers and acts as a waveguide. The dielectric thin film 60 is formed of a dielectric material, such as $SiO_2$, $Al_2O_3$, $TiO_2$, $MgF_2$, and ZnS, to a thickness of 400–800 nm. Unlike the SPR sensor where surface plasmon waves propagate along the surface of the metal thin film 22, the incident light beam 31 is coupled into the surface plasmon mode between the surface of the metal thin film 22 and the dielectric thin film 60 deposited on the metal thin film 22 and propagates along the dielectric thin film 60. In the CPWR sensor having the configuration above, the CPWR or attenuated total reflection (ATR) leaky mode is observed at an angle smaller than the resonance angle of the SPR sensor.

FIG. 4 shows reflectances as a function of the incident angle of light measured using the CPWR sensor of FIG. 3 for samples of different refractive indices. In FIG. 4, (1) is for water, (2) is for a sample with a refractive index difference of $10^{-6}$ from water, and (3) is for a sample with a refractive index difference of $10^{-3}$ from water, as in FIG. 2.

As shown in FIG. 4, the CPWR sensor has a narrower range of resonance angle than the SPR sensor. Thus, the CPWR sensor is expected to be able to easily measuring changes in resonance angle for the samples of different refractive indices, compared to the SPR sensor. Actually, the CPWR sensor can measure the amount of protein adsorbed to a sample surface to a concentration of 0.5 pg/mm² with 2–4 times improvement in resolution compared to the SPR sensor.

As shown in an inset for a portion A in FIG. 4, a change in resonance angle ($\Delta\theta$) by about 0.00008° occurs between samples (1) and (2) having a refractive index difference of $10^{-6}$. Because the CPWR sensor of FIG. 3 also has an angular resolution limit of about 0.0001°, there is a need to improve the resolution of refractive index by using the rotary plate 50 or a multi-channel photodetector, such as a PDA, as the photodetector 40, which is capable of improve the angular resolution. However, technical problems hinder use of this approach. Moreover, aside from technical difficulties, due to the high cost involved, this approach is not economically feasible.

When reflectances are measured at a fixed incident angle $\beta$ using the CPWR sensor of FIG. 4, a change in reflectance ($\Delta R$) for a refractive index difference of $10^{-6}$ between samples is about 0.56% at $\beta=61.5665°$, which is greater than the conventional SPR sensor. This result supports that the resolution of refractive index can be improved by increasing changes in reflectance with respect to incident angle variations, i.e., the slope of a curve of reflectance versus incident angle, by making the range of resonance angle narrow.

Theoretically, changes in reflectance with respect to incident angle variations can be increased by reducing the thickness of the dielectric thin film in the CPWR sensor. However, improving the resolution of refractive index by this method has limitations for the following reasons.

FIG. 5A shows reflectances as a function of the incident angle measured using CPWRs having different dielectric film thicknesses. In FIG. 5A, (a), (b), and (c) are for the cases where the dielectric thin film, for example, formed of $TiO_2$, has a thickness of 138 nm, 135 nm, and 133 nm, respectively.

Referring to FIG. 5A, when the dielectric thin film is deposited to a thickness as small as 138 nm or less, the measurable range of reflectance becomes narrow, so it is difficult to select an appropriate incident angle. Finally, the width of resonance dip becomes partially broad at a dielectric film thickness of 133 nm. Therefore, improving the resolution of refractive index in the reflectance measurement method through the adjustment of dielectric film thickness is limited.

FIG. 5B shows absorbances as a function of the incident angle of light measured using CPWRs having different dielectric film thicknesses. In FIG. 5B, (a), (b), and (c) are for the cases where the dielectric thin film, for example, formed of $TiO_2$, has a thickness of 138 nm, 135 nm, and 133 nm, respectively, as in FIG. 5A.

As shown in FIG. 5B, the pattern of the absorbance curve is maintained at a reduced dielectric film thickness of 133 nm with a steep slope portion as indicated by "A". Therefore, a sensor with improved refractive index resolution can be implemented by measuring changes in absorbance, rather than reflectance, with respect to refractive index variations, at least within the range of the incident angle for the step slope portion "A". However, the absorbance of the metal thin film cannot be measured using the CPWR sensor having the above-described structure.

SUMMARY OF THE INVENTION

To solve the above-described problems, it is an objective of the present invention to provide an active ion-doped waveguide-plasmon resonance (AID WPR) sensor with improved sensitivity over the conventional surface plasmon resonance (SPR) sensor and coupled plasmon-waveguide resonance (CPWR) sensor, and an imaging system based on the principle of the active ion-doped waveguide-plasmon resonance sensor.

To achieve the objective of the present invention, unlike the conventional SPR or CPWR sensor, which measures the resonance angle from the intensity of reflected light (reflectance) received by a photodetector with angular resolution, such as a photodiode array (PDA) or a photodetector which is supported by a rotary plate, a method of measuring the absorption of an incident light beam through surface plasmon resonance is used. The active ion-doped waveguide-plasmon resonance (AID WPR) according to the present invention is characterized in that it uses a dielectric thin film doped with active ions of an element or organic dye capable of fluorescing through absorption of an incident light beam, in proportional to the intensity of the absorbed light beam, and determines the absorption of the incident light beam from fluorescence variations of the active ions with improved refractive index resolution of samples.

In particular, the AID WPR sensor according to the present invention includes a conductive thin film for providing surface plasmons and a dielectric medium disposed at one side of the conductive thin film. A light source emits an incident light beam to the conductive thin film through the dielectric medium. A dielectric thin film having a surface to which a sample is attached is deposited at the surface of the conductive thin film opposite to the dielectric medium. The dielectric thin film is doped with active ions capable of fluorescing by being excited by the incident light beam. A photodetector receives and measures the intensity of fluorescence from the active ions to determine variations in refractive index for a sample. Quantification and qualification of the sample or measurement of the thickness of the sample (if the sample is a thin film) can be achieved from the refractive index variations.

Suitable photodetectors include a photodiode, a photomultiplier (PMT), a charge coupled device (CCD), and a photosensitive sheet. When the conductive thin film and the dielectric thin film are formed as arrays having a grid pattern, and a CCD or photosensitive sheet is used as the photoreceptor, an imaging system that images the sample with the contrast based upon fluorescence intensity variations between each array can be implemented.

In the AID WPR sensor and the imaging system using the same according to the present invention, the dielectric medium may be formed as a trapezoidal prism, and an optical filter or a lens may be further included. The trapezoidal prism is for directing the fluorescence in diverging directions toward the photodetector, and the optical filter enables the photodetector to receive pure light from the active ions by filtering out the wavelength of the incident light beam. The lens condenses the light from the active ions toward the photodetector.

Preferably, the active ions are derived from one selected from the group consisting of transition metal, rare-earth element, and organic dye. Preferably, the active ions have the ability to fluoresce by emitting light of a shorter wavelength than the incident light beam through two-photon or three-photon absorption. Suitable active ions include $Tm^{3+}$ ions, $Er^{3+}$ ions, $Yb^{3+}$ ions, $Ho^{3+}$—$Yb^{3+}$ composite ions, $Tm^{3+}$—$Yb^{3+}$ composite ions, $Er^{3+}$—$Yb^{3+}$ composite ions, and $Tm^{3+}$—$Nd^{3+}$ composite ions. The wavelengths of the incident light beam and the light emitted from active ions are determined according to the type of active ions embedded in the dielectric thin film.

Preferably, the dielectric thin film is formed to be thick enough to produce a coupled plasmon-waveguide resonance mode and attenuated total reflection leaky mode coupled to surface plasma resonance, for example, to have a thickness of 100–700 nm.

BRIEF DESCRIPTION OF THE DRAWINGS

The above objective and advantages of the present invention will become more apparent by describing in detail preferred embodiments thereof with reference to the attached drawings in which.

DETAILED DESCRIPTION OF THE INVENTION

Figure 1:
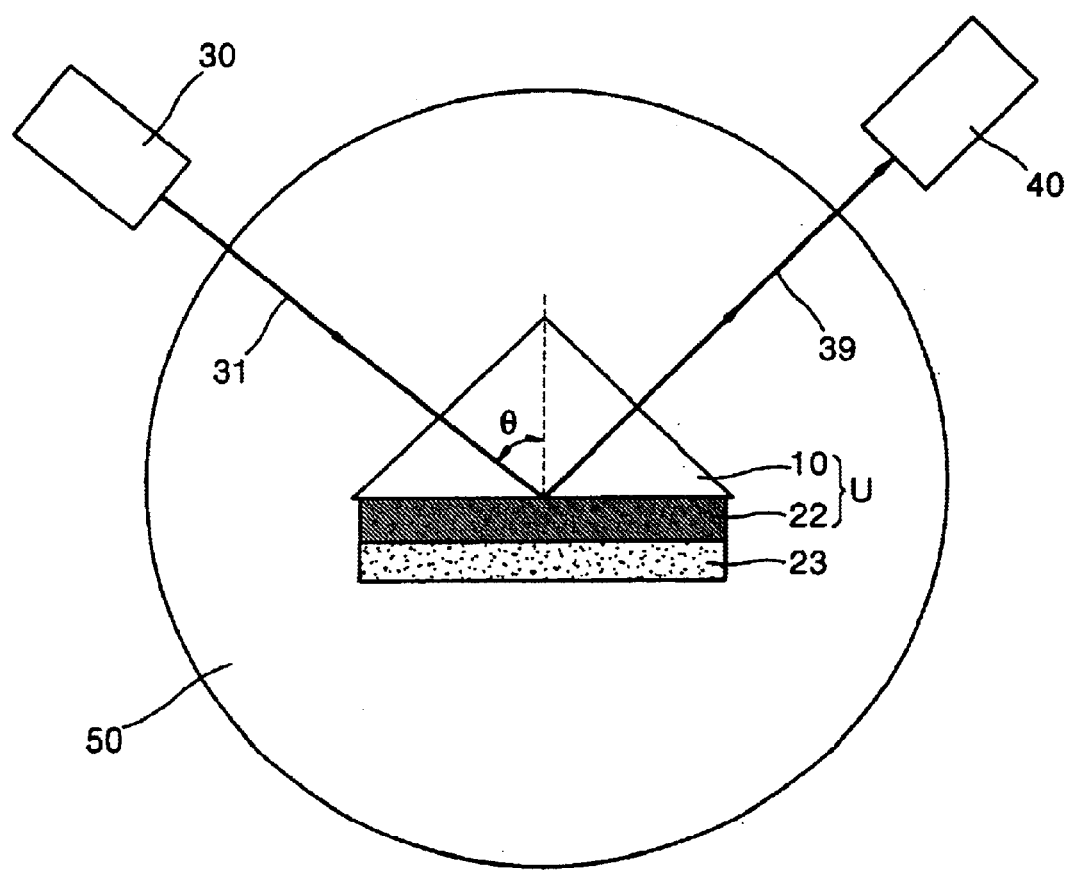
FIG. 1 shows the structure of a typical surface plasmon resonance (SPR) sensor.
Figure 2:
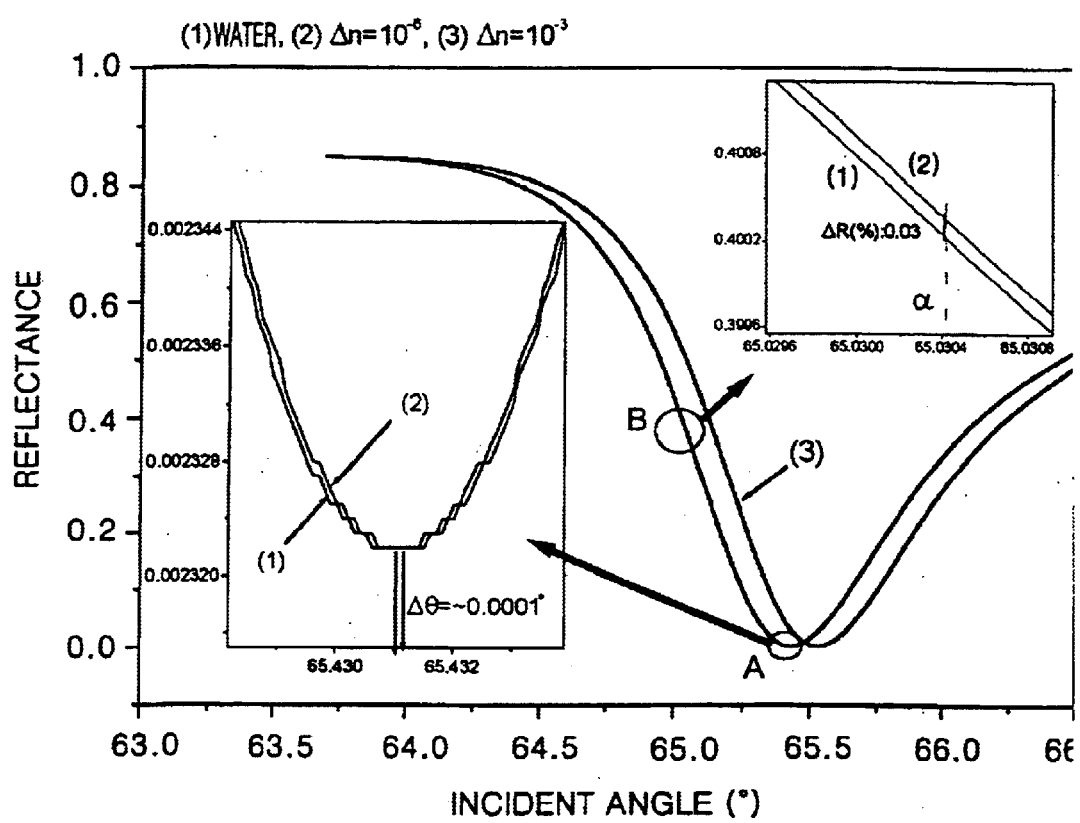
FIG. 2 shows reflectances as a function of the incident angle of light measured using the SRP sensor of FIG. 1 for the samples of different refractive indices.
Figure 3:
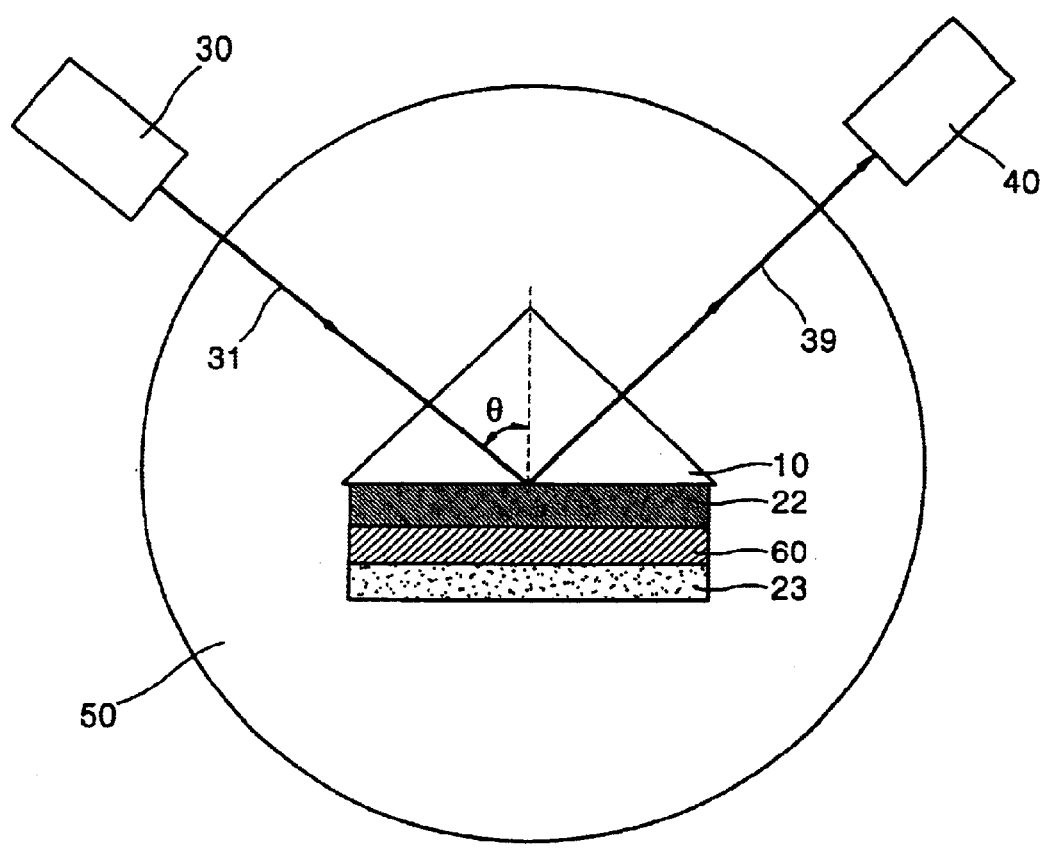
FIG. 3 shows the structure of a coupled plasmon-waveguide resonance (CPWR) sensor improved from the SPR sensor of FIG. 1.
Figure 4:
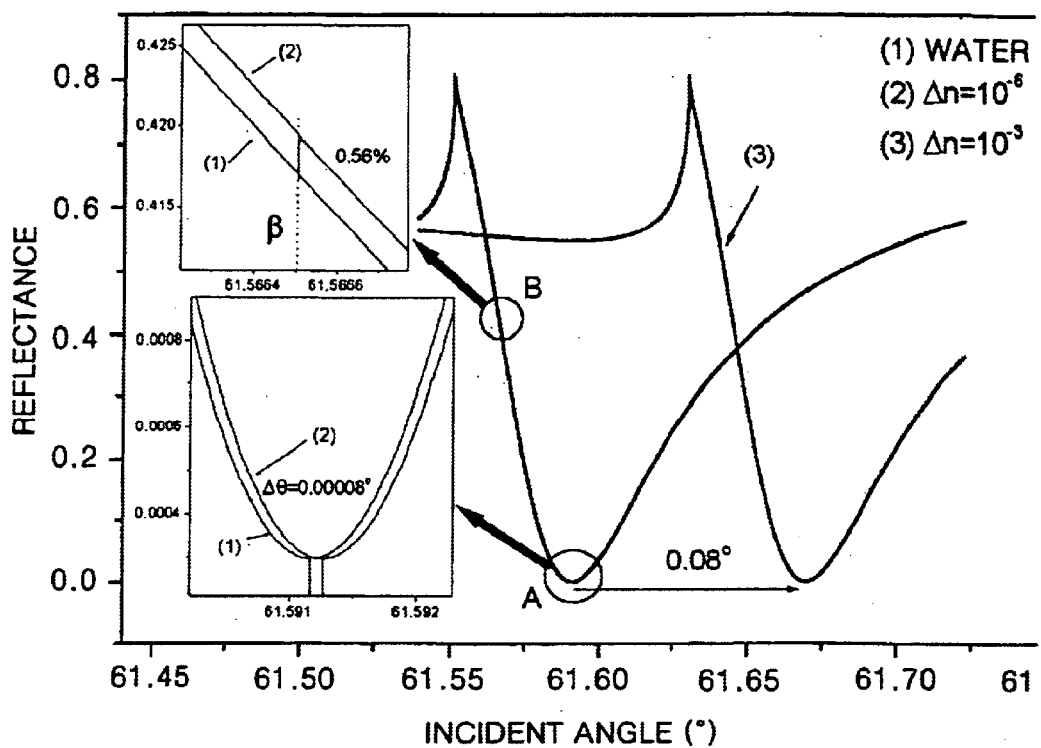
FIG. 4 shows reflectances as a function of the incident angle of light measured using the CPWR sensor of FIG. 3 for the samples of different refractive indices.
Figure 5A:
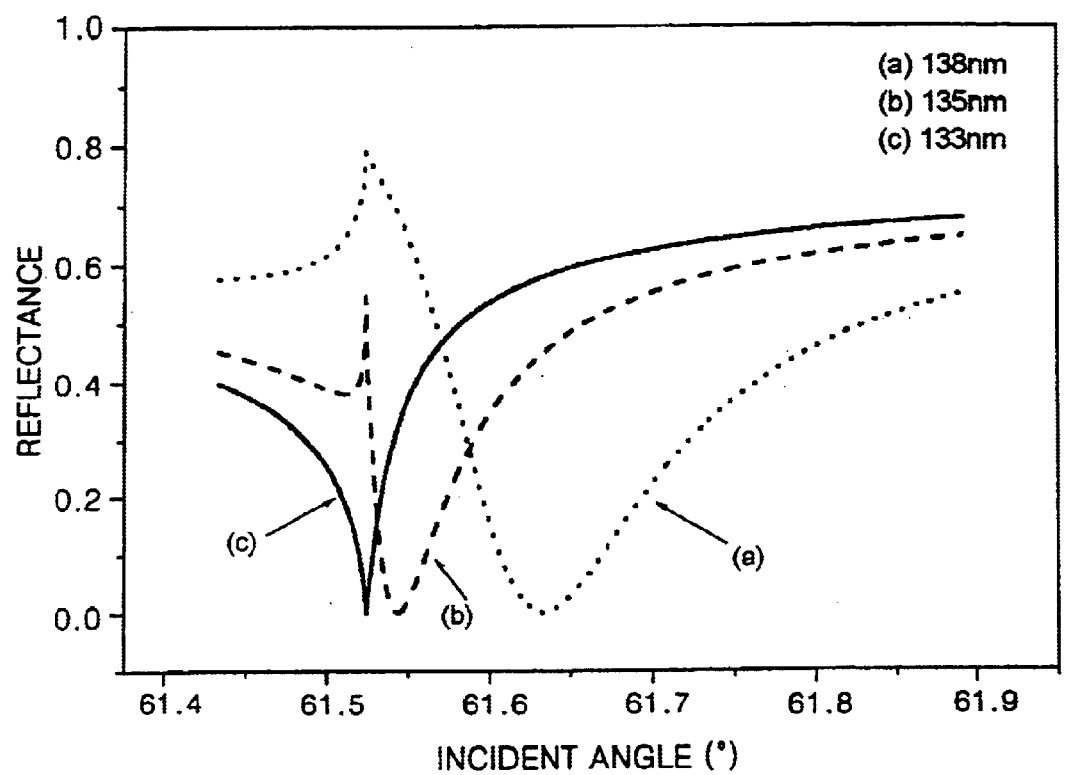
FIG. 5A shows reflectances as a function of the incident angle measured using CPWRs having different dielectric film thicknesses.
Figure 5B:
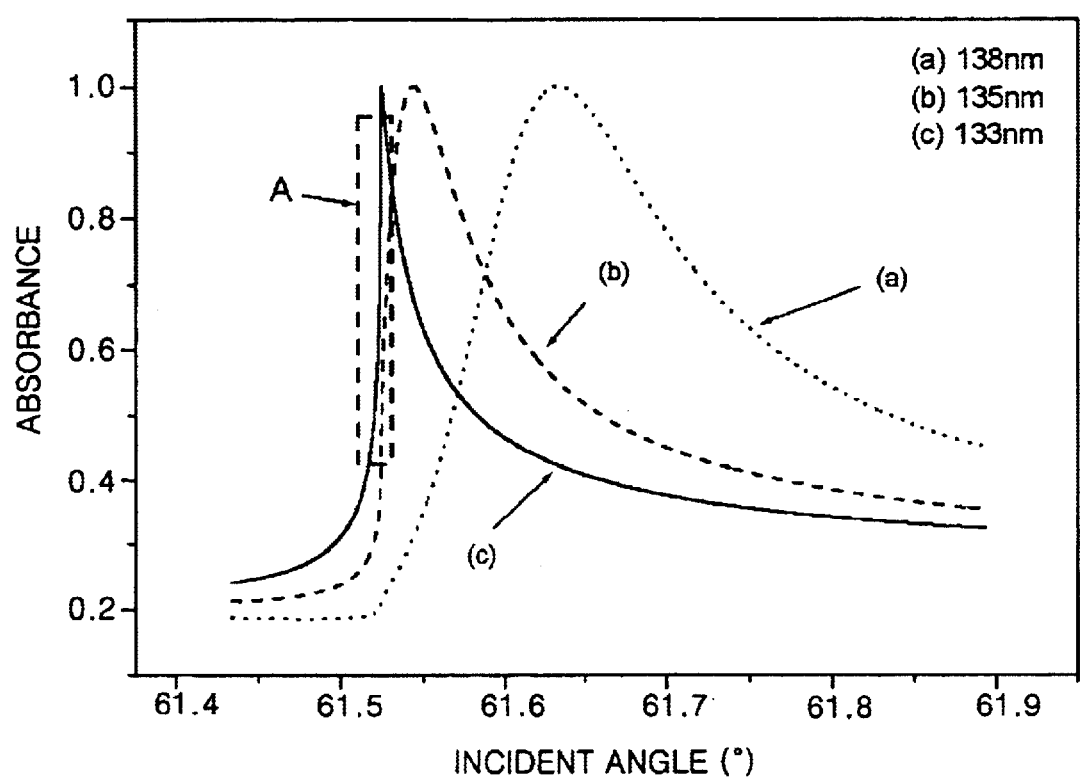
FIG. 5B shows absorbances as a function of the incident angle of light measured using CPWRs having different dielectric film thicknesses.

The present invention now will be described more fully with reference to the accompanying drawings, in which preferred embodiments of the invention are shown. This invention may, however, be embodied in many different forms and should not be construed as being limited to the embodiments set forth herein; rather, these embodiments are provided so that this disclosure will be thorough and complete, and will fully convey the concept of the invention to those skilled in the art. In the drawings, a variety of elements and regions are schematically illustrated and thus the present invention is not limited by relative sizes and intervals in the drawings. It is also noted that like reference numerals may be used to designate identical or corresponding parts throughout the several views.

Figure 6:
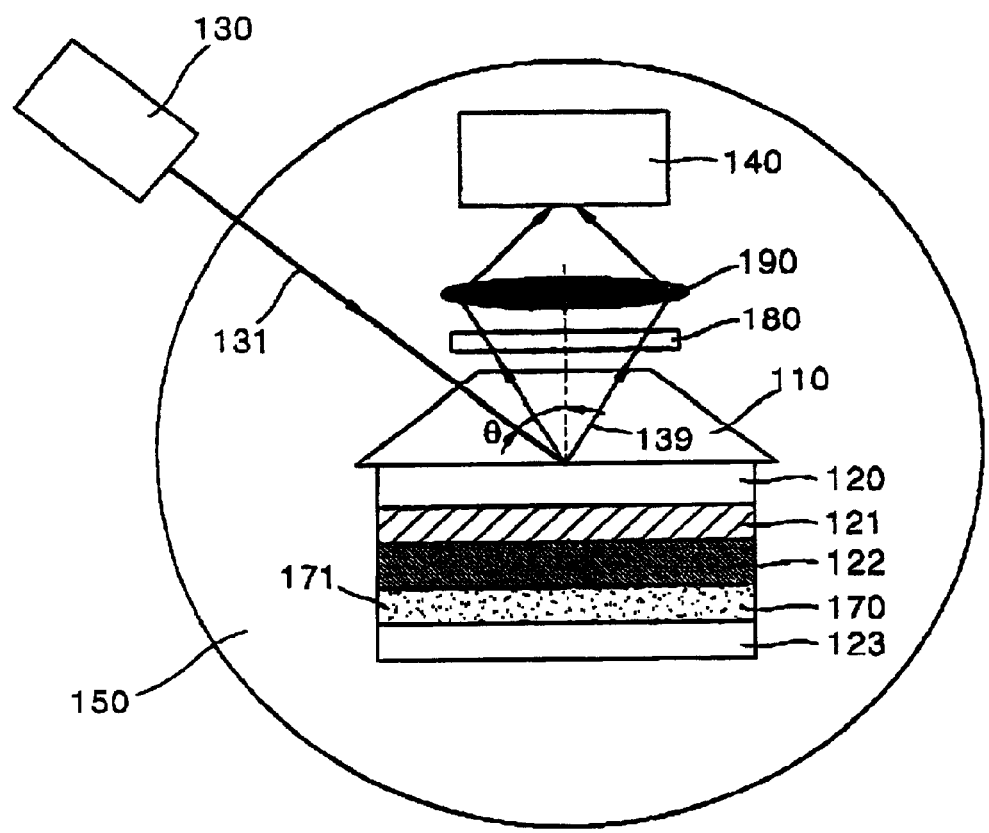
FIG. 6 shows the structure of an active ion-doped waveguide-plasmon resonance (AID WPR) sensor according to a preferred embodiment of the present invention.

FIG. 6 shows the structure of an active ion-doped waveguide-plasmon resonance (AID WPR) sensor according to a preferred embodiment of the present invention. Referring to FIG. 6, the AID WPR sensor according to the preferred embodiment of the present invention includes a conductive thin film 122 for providing surface plasmon and a dielectric medium 110 disposed at one side of the conductive thin film 122. A light source 130 emits an incident light beam 131 to the conductive thin film 122 through the dielectric medium 110. A dielectric thin film 170 is deposited at the surface of the conductive thin film 122 opposite to the dielectric medium 110 and a sample 123 is brought into contact with the dielectric thin film 170. Active ions 171 capable of fluorescing by emitting light 139 by being excited with the incident light beam 131 is embedded in the dielectric thin film 170. A photodetector 140 receives the light 139 from the active ions 171 and measures its intensity in order to measure changes in the refractive index of the sample 123, which enables quantification and qualification of the sample 123 or measurement of the thickness of the sample 123.

The conductive thin film 122 may be one selected from the group consisting of gold (Au), silver (Ag), copper (Cu), silicon (Si), and germanium (Ge), and may have a thickness of 35–50 nm. The conductive thin film 122 may be previously deposited on the bottom of the glass substrate 121 for installation into the AID WPR sensor according to the present invention. Preferably, a chromium (Cr) layer or titanium (Ti) layer (not shown) having a thickness of about 2–4 nm is deposited on the glass substrate 121 before deposition of the conductive layer 122 to improve adhesion between the glass substrate 121 and the conductive thin film 122.

The dielectric medium 110 is formed on top of the glass substrate 121, preferably, with an index matching oil layer 120 between the dielectric medium and the glass substrate 121. Preferably, the dielectric medium 110 is formed as a trapezoidal prism for directing the light 139 in diverging directions to the photodetector 140. The incident light beam 131 propagates through the dielectric medium 110, the index matching oil layer 120, and the glass substrate 121 which have the same refractive index and is incident onto the surface of the conductive thin film 122 at an incident angle θ.

The sample 123 can be gaseous, liquid, or solid. If the sample 123 is liquid, additional devices (not shown) such as a sample holder and a pump for sample circulating are required. However, if the sample 123 is solid, no additional device is required.

In the preferred embodiment of the AID WPR sensor according to the present invention, the incident light beam 131 is incident onto the conductive thin film 122 through the dielectric medium 110, the index matching oil layer 120, and the glass substrate 121 at a particular incident angle θ at which coupled plasmon-waveguide resonance (CPWR) occurs and then coupled to propagate into the dielectric thin film 170, thereby exciting the active ions 171 embedded in the dielectric thin film 170. Then, the intensity of the light 139 emitted from the active ions 171 is measured. In FIG. 6, the light 130 appears to be emanating from the interface between the dielectric medium 110 and the index matching oil layer 120 for convenience. The intensity of the light 139 varies depending on the kind, amount, refractive index, and thickness (if the sample is a thin film) of the sample 123, and thus such properties of the sample 123 can be analyzed from the fluorescent intensity variations.

It is preferable that the light source 130 emits a transverse magnetic (TM) polarized light or transverse electric (TE) polarized light. To enable emission of such a polarized light, the light source 130 is constructed of a light emitter and a polarization device (not shown). It is preferable that a light source capable of emitting a monochromatic parallel light beam is selected as the light source 130. A typical example of the light source emitting a monochromic parallel light beam is a laser. The incident light beam 131 is incident onto the conductive thin film 122 at a fixed incident angle. Alternatively, the intensity of the light 139 can be measured while rotating the rotary plate 150 to vary the incident angle.

A photodiode, photomultiplier (PMT), charge coupled device (CCD), or photosensitive sheet can be used as the photodetector 140. Preferably, the light 139 is allowed to pass an optical filter 180 and a lens 190 before reaching the photodetector 140. The wavelength of the incident light beam 131 is filtered off by the filter 180 and the light 139 passed through the filter 180 is condensed by the lens 190 and received by the photodetector 140 with improved purity.

The dielectric thin film 170 may be one selected from the group consisting of $SiO_2$ layer, $Al_2O_3$ layer, $TiO_2$ layer, $Ta_2O_5$ layer, $MgF_2$ layer, $Y_2O_3$ layer, $TeO_2$ layer, PbO layer, $LaF_3$ layer, ZnS layer, ZnSe layer, $Si_3N_4$ layer, AlN layer, or a composite layer of these layers. The active ions 171 embedded in the dielectric thin film 170 may be selected from the group consisting of transition metal, rare-earth element, organic dye. The active ions 171 derived from, for example, a transition metal, rare-earth element, and organic dye can emit the light 139 having a shorter wavelength than the incident light beam 131 by upconversion through two-photon or three-photon absorption. Thus, for example, if an infrared or red exciting light is incident, a visible or UV ray having a shorter wavelength than the incident light beam can be emitted.

The dielectric thin film 170 doped with the active ions 171 is deposited on the conductive thin film 122 as follows. When the active ions 171 of a rare-earth element or transition metal are used, the dielectric thin film 170 is deposited on the conductive thin film 122 by electron-beam vacuum evaporation or thermal evaporation. In this case, a precursor containing a desired active ion is required. When such a precursor is not commercially available, which is usually the case, a desired precursor is prepared for use by a sol-gel method and high-temperature sintering. When the active ions 170 derived from an organic dye is used, the precursor is prepared by a wet method such as a sol-gel method and then deposited on the conductive thin film 122 by dip coating or spin coating.

As the thickness of the dielectric thin film 170 doped with the active ions 171 is increased, the resonance angle becomes larger and goes beyond the observable range of the conventional SPR sensor. As the thickness of the dielectric thin film 170 is increased further, a CPWR or attenuated total reflection (ATR) leaky mode, i.e., TE or TM mode, appears depending on the polarization (TE- or TM-polarization) of the incident light beam 131. When a non-polarized light source is used, the TE mode and the TM mode appear alternately. The thickness of the dielectric thin film 170 doped with the active ions 171 should be appropriately determined to enable propagation of both modes, for example, in the range of about 100–700 nm, depending on the wavelength of the incident light beam 131 and the refractive index of the dielectric thin film 170.

$Tm^{3+}$ ions as an example of the active ions 171, have been of interest in research associated with infrared laser and UV upconversion light source. Also, this rare-earth element has recently been found to be available a source of active ions for a 1.4 $\mu$m-wavelength optical fiber amplifier and becomes more interesting in the field of optical communications. Another example of the active ions 171 is $Er^{3+}$ ions, which are derived from the most interesting rare-earth element used for erbium-doped fiber amplifiers (EDFAs) in the field of optical communications. In the preferred embodiment of the AID WPR sensor according to the present invention, $Yb^{3+}$ ions, $Ho^{3+}$—$Yb^{3+}$ composite ions, $Tm^{3+}$—$Yb^{3+}$ composite ions, $Er^{3+}$—$Yb^{3+}$ composite ions, and $Tm^{3+}$—$Nd^{3+}$ composite ions, as well as $Tm^{3+}$ and $Er^{3+}$ ions can be used as the active ions 171.

Figure 7:
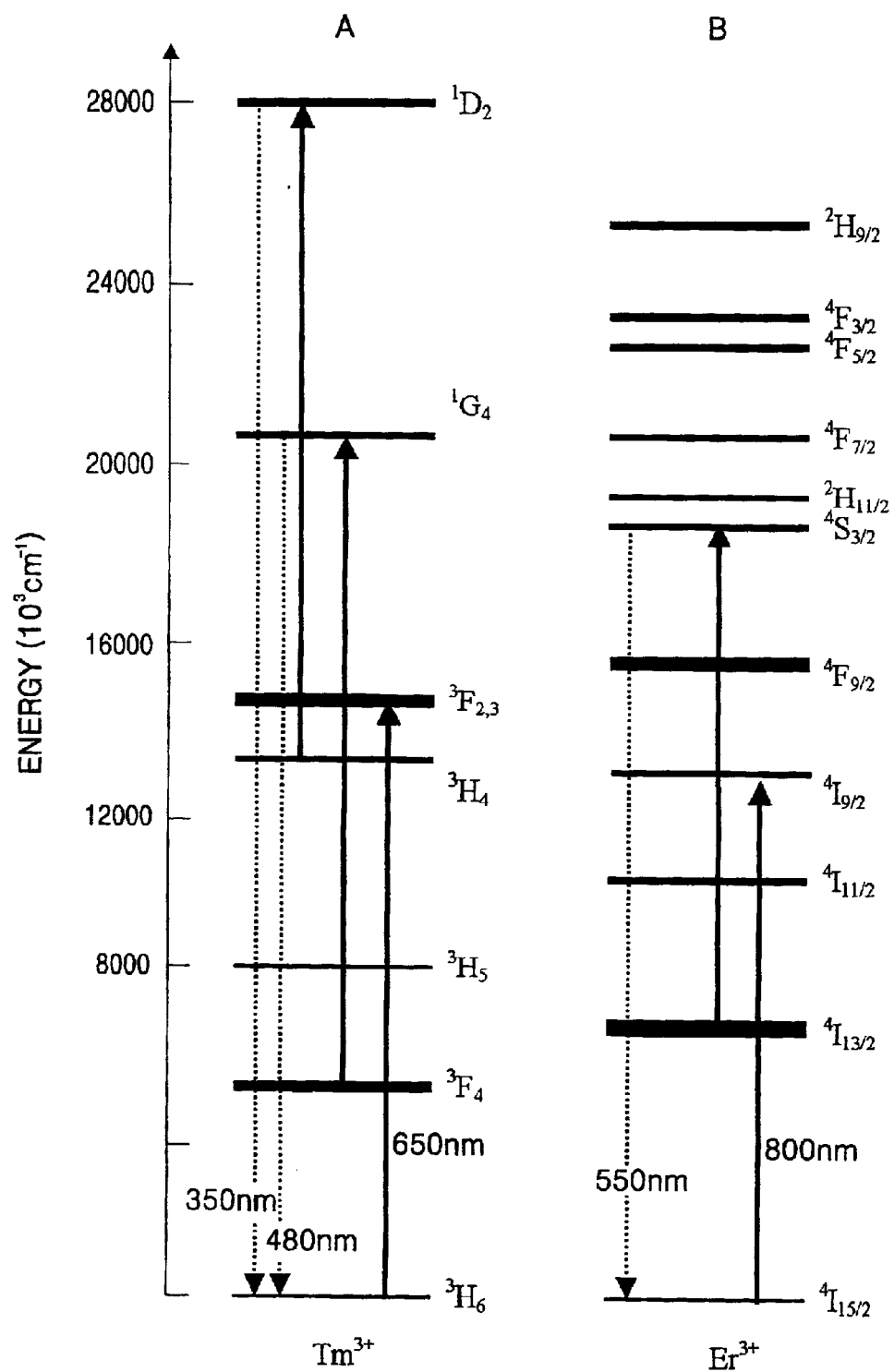
FIG. 7 illustrates the energy levels and upconversion mechanism of $Tm^{3+}$ and $Er^{3+}$ ions.

FIG. 7 illustrates the energy levels and upconversion mechanism of $Tm^{3+}$ and $Er^{3+}$ ions. In particular, for $Tm^{3+}$ indicated by "A" in FIG. 7, $Tm^{3+}$ is excited from the ground level, $^3H_6$ energy level, to energy level $^3F_{2,3}$ by absorption of a 650-nm incident light (Step 1). The excited $Tm^{3+}$ spends its intrinsic fluorescence lifetime in energy level $^3F_{2,3}$ and decays to energy level $^3H_4$ and $^3H_5$ or $^3F_4$ through radiative and non-radiative transitions. In Step 2, the $Tm^{3+}$ at energy level $^3H_4$ and $^3H_5$ or $^3F_4$ is excited to energy level $^1G_4$ or $^1D_2$ by absorption of the 650-nm incident light and subsequently returns to the ground level $^3H_6$ by spontaneous transition, emitting 480-nm blue light and 350-nm UV light, respectively. In Step 3, some electrons at energy level $^1G_4$ of $Tm^{3+}$ transit to energy level $^3H_4$ directly or via the next lower energy level $^3F_{2,3}$ and are then excited to energy level $^1D_2$ by absorption of the 650-nm incident light, and return to the ground level, emitting 350-nm UV light.

In Step 2, the intensity of the fluorescence through two-photon absorption of the incident light is proportional to the square of intensity of the incident light. In Step 3, the intensity of the fluorescence through three-photon absorption of the incident light is proportional to the cube of intensity of the incident light. The intensity of 350-nm UV emission caused by transition from energy level $^1D_2$ to the ground level is proportional to the square of intensity of the incident light for a weak incident light beam and to the cube of intensity of the incident light for a strong incident light beam. When the fluorescence intensity of active ions varies in proportional to the square or the cube of the intensity of the incident light, the intensity of an incident light beam propagating the dielectric thin film 170 doped with $Tm^{3+}$ varies for changes in the refractive index of the sample 123, and the fluorescence intensity of the light 139 from $Tm^{3+}$ at a wavelength of 350 nm by upconversion varies in proportional to the square or the cube of intensity of the incident light beam 131. Therefore, variations in the fluorescence intensity of the light 139 can be measured sensitively, even for a minor change in the refractive index of the sample, with improved refractive index resolution.

550-nm visible light can be emitted through two-photon upconversion of $Er^{3+}$ ions by excitation with an 800-nm incident light beam, as indicated by "B" in FIG. 7. $Er^{3+}$ ions are excited from the ground state to energy level $^4I_{9/2}$ by absorption of the 800-nm incident light beam. Embedded in most dielectric oxides having a high fundamental vibration frequency, the $Er^{3+}$ ions nonradiatively transit to energy level $^4I_{13/2}$ through multiphonon relaxation. The fluorescence lifetime of $Er^{3+}$ in energy level $^4I_{13/2}$ is as long as several milliseconds so that the $Er^{3+}$ ions are excited to energy level $^4S_{3/2}$ through secondary absorption or excited state absorption of the incident light beam and subsequently returns to the ground level by radiative transition, emitting 550-nm visible light.

The wavelengths of the incident light beam 131 and the light 139 emitted from the active ions 171 are determined depending on the type of the active ions 171 embedded in the dielectric thin film 170. As described above, when $Tm^{3+}$ ions are used as the active ions 171, a light beam of 650 nm is selected as the incident light beam 131 and thus 350-nm light is emitted. When $Er^{3+}$ ions are used as the active ions 171 and the wavelength of the incident light beam 131 is 800 nm, 550-nm light is emitted. When $Yb^{3+}$ ions are used as the active ions 171 and the wavelength of the incident light beam 131 is 980 nm, 480-nm light is emitted. When $Ho^{3+}$—$Yb^{3+}$ composite ions are used as the active ions 171 and the wavelength of the incident light beam 131 is 980 nm, 550-nm light is emitted. When $Tm^{3+}$—$Yb^{3+}$ composite ions are used as the active ions 171 and the wavelength of the incident light beam 131 is 980 nm, 480-nm light is emitted. When $Er^{3+}$—$Yb^{3+}$ composite ions are used as the active ions 171 and the wavelength of the incident light beam 131 is 980 nm, 550-nm light is emitted. When $Tm^{3+}$—$Nd^{3+}$ composite ions are used as the active ions 171 and the wavelength of the incident light beam 131 is 800 nm, 480-nm light is emitted.

Figure 8A:
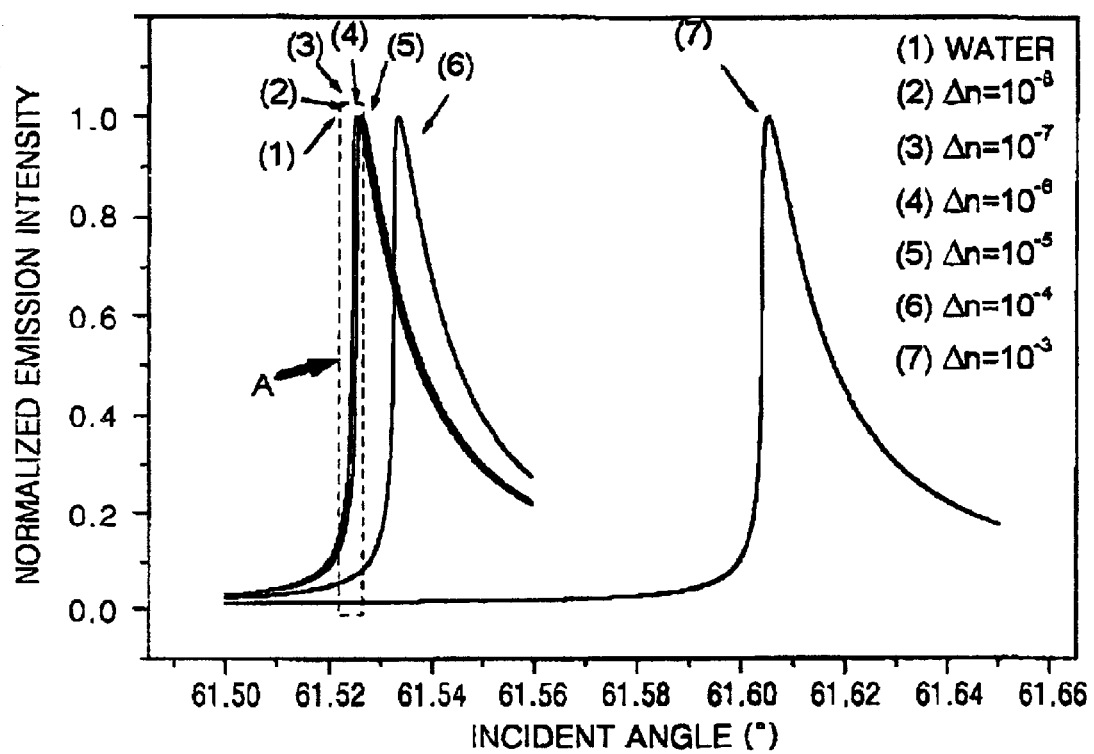
FIG. 8A shows the intensity of 350-nm fluorescence through upconversion of $Tm^{3+}$ ions with respect to incident angle variations for the samples of different refractive indices.
Figure 8B:
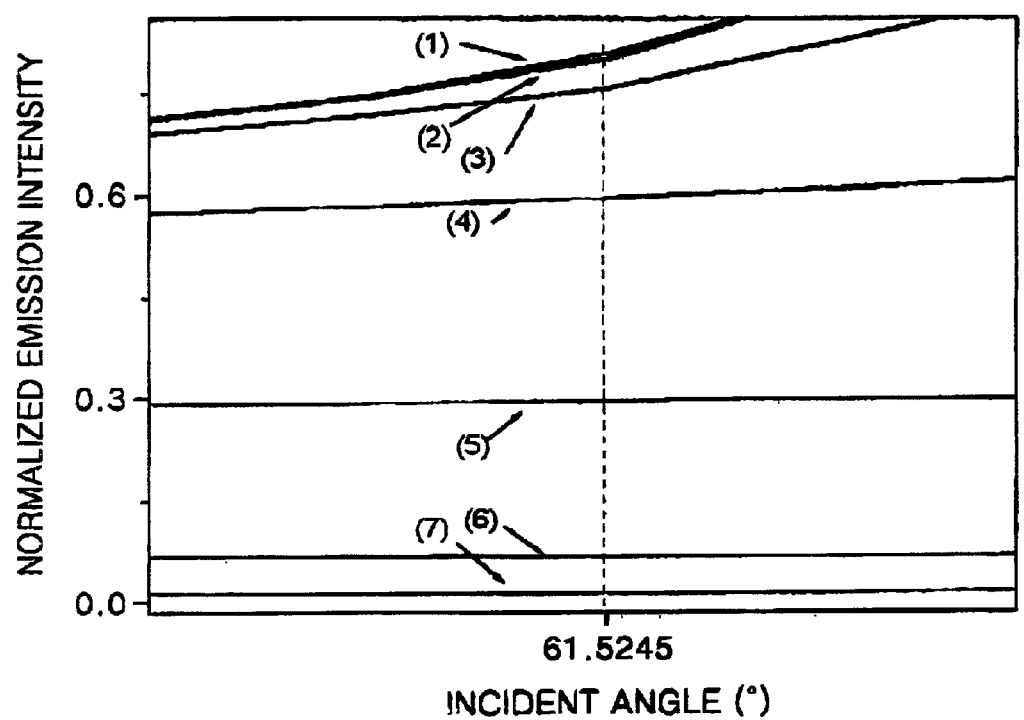
FIG. 8B is an enlarged view of region A in FIG. 8A.
Figure 8C:
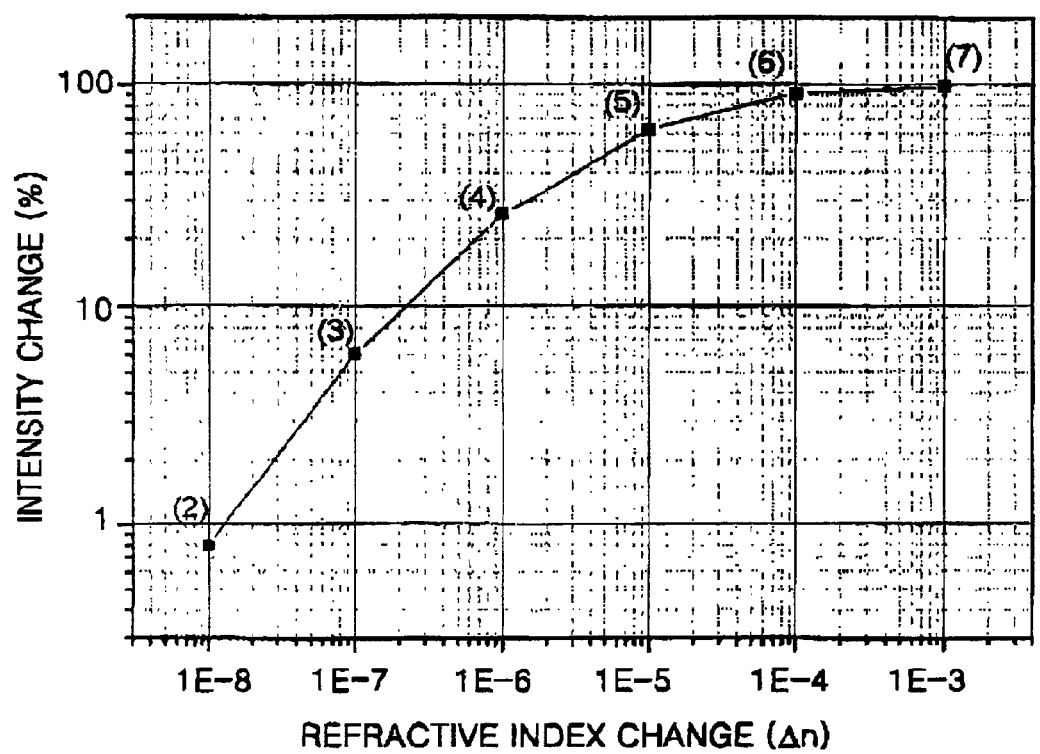
FIG. 8C shows relative variations in the 350-nm fluorescence intensity of $Tm^{3+}$ at a fixed incident angle of 61.52455° for the samples of different refractive indices.

FIG. 8A shows the intensity of fluorescence with respect to incident angle variations for the samples of different refractive indices when a 133-nm-thick $TiO_2$ layer is used as the dielectric thin film 170, $Tm^{3+}$ ions are used as the active ions 171, and 350-nm fluorescence through upconversion is induced with a 650-nm incident light beam. FIG. 8B is an enlarged view of region A in FIG. 8A. In FIGS. 8A and 8B, (1) is for water, and (2), (3), (4), (5), (6), and (7) are for samples having a refractive index difference of $10^{-8}$, $10^{-7}$, $10^{-6}$, $10^{-5}$, $10^{-4}$ and $10^{-3}$ respectively, with respect to water (1). FIG. 8C shows relative variations in the 350-nm fluorescence intensity of $Tm^{3+}$ at a fixed incident angle of 61.5245° for samples (2) through (7) with respect to water (1). For this measurement, a titanium layer having a thickness of about 2 nm was deposited on the glass substrate 121 and the conductive thin film 122 having a thickness of 45 nm was formed of silver.

Referring to FIG. 8C, a variation of 0.8% in fluorescence intensity was observed for a minor refractive index variation of $10^{-8}$. Considering the optical signal resolution of a common photoreceptor is about 0.2%, it is evident that a minor change in reflective index can be detected using the AID WPR sensor according to the present invention.

Figure 9A:
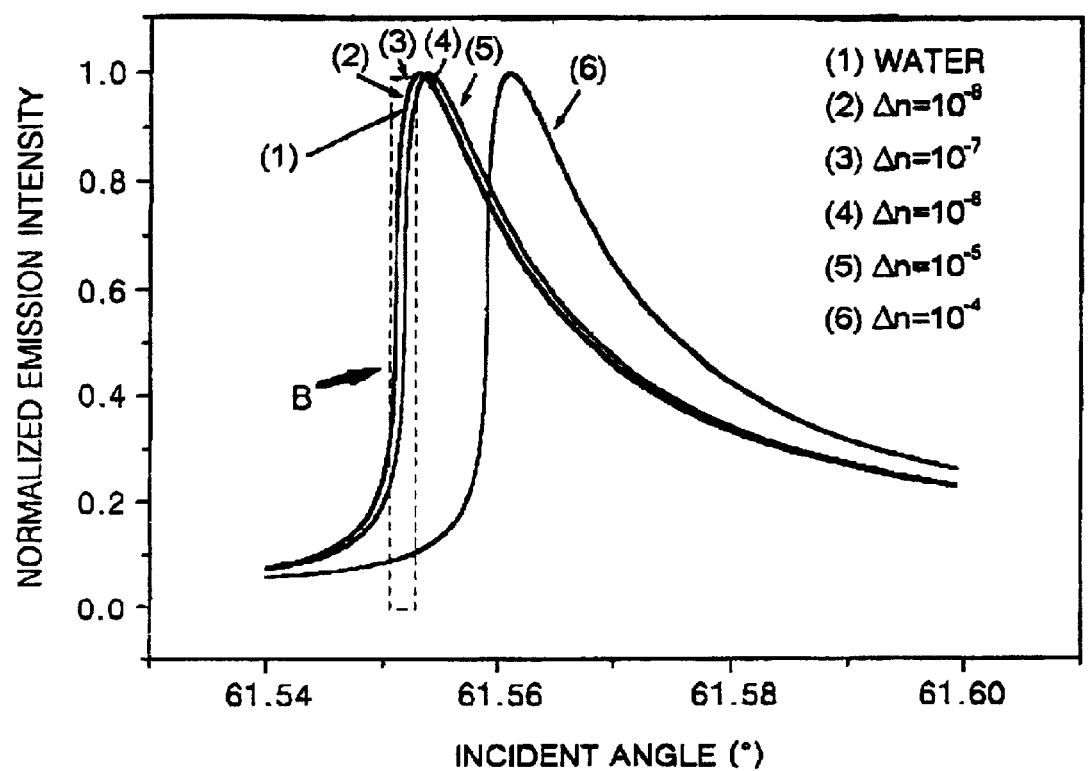
FIG. 9A shows the intensity of 550-nm fluorescence through upconversion of $Er^{3+}$ ions with respect to incident angle variations for the samples of different refractive indices.
Figure 9B:
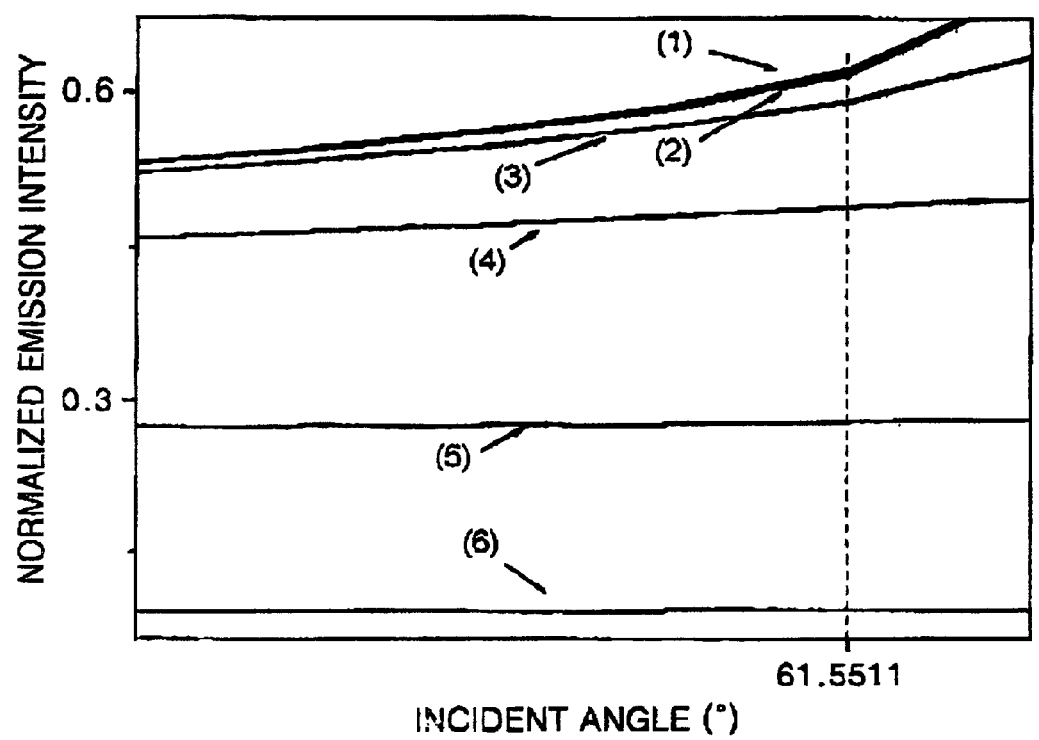
FIG. 9B is an enlarged view of region A in FIG. 9A.
Figure 9C:
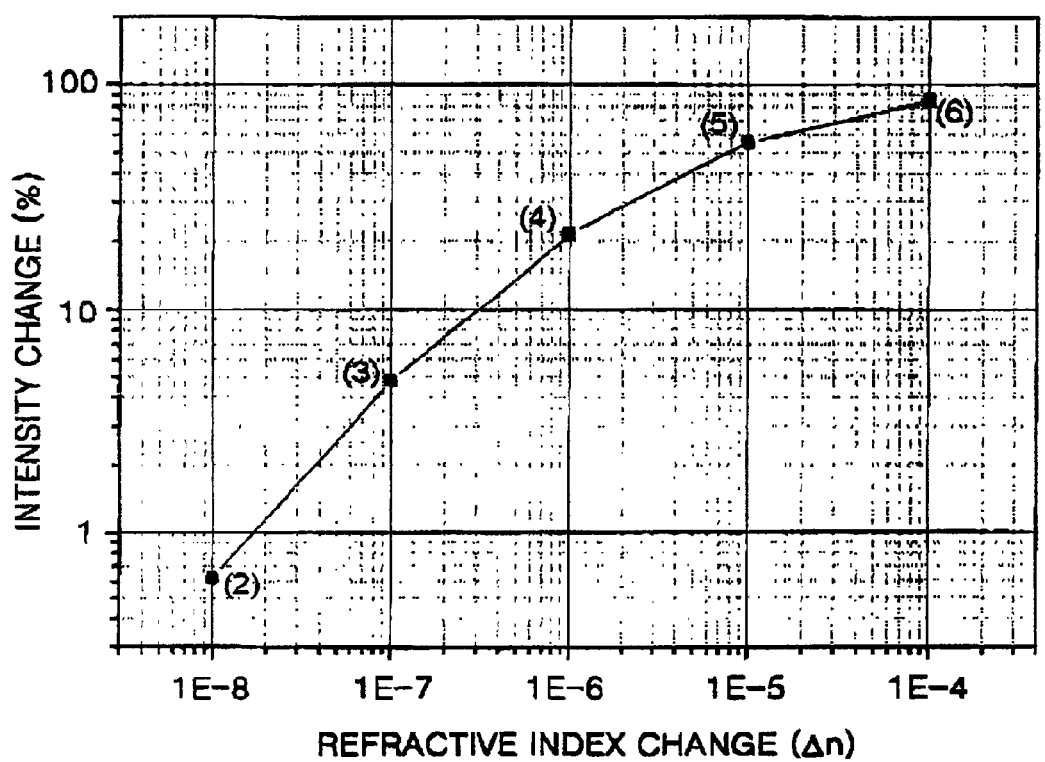
FIG. 9C shows relative variations in the 550-nm fluorescence intensity of $Er^{3+}$ at a fixed incident angle of 61.5511° for the samples of different refractive indices.

FIG. 9A shows the intensity of fluorescence with respect to incident angle variations for the samples of different refractive indices when a 183-nm-thick $TiO_2$ layer is used as the dielectric thin film 170, $Er^{3+}$ ions are used as the active ions 171, and 550-nm fluorescence through upconversion is induced with an 800-nm incident light beam. FIG. 9B is an enlarged view of region B in FIG. 9A. In FIGS. 9A and 9B, (1) is for water, and (2), (3), (4), (5), and (6) are for samples having a refractive index difference of $10^{-8}$, $10^{-7}$, $10^{-6}$, $10^{-5}$, and $10^{-4}$, respectively, with respect to water (1). FIG. 9C shows relative variations in the 550-nm fluorescence intensity of $Er^{3+}$ at a fixed incident angle of 61.5511° for samples (2) through (6) with respect to water (1). For this measurement, a titanium layer having a thickness of about 2 nm was deposited on the glass substrate 121 and the conductive thin film 122 having a thickness of 45 nm was formed of silver.

Referring to FIG. 9C, a variation of 0.6% in fluorescence intensity was observed for a minor refractive index variation of $10^{-8}$. Considering the optical signal resolution of a common photoreceptor is about 0.2%, it is evident that a minor change in reflective index can be detected using the AID WPR sensor according to the present invention.

According to the present invention, upconversion of the active ions 171 is coupled with surface plasmon resonance upon excitation with the incident light beam 131, thereby resulting in the light 139 of a shorter wavelength than the incident light beam 131. As a result, the fluorescence intensity of the active ions 171 is greatly varied according to changes in the incident angle of the incident light beam 131 with about 100 times greater sensitivity than the conventional SPR sensor. Therefore, a minor change in the refractive index of a sample, which cannot be detected using the conventional SPR sensor, or a trace adsorbed material can be quantitatively a measured using the AID WPR sensor according to the present invention.

Figure 10:
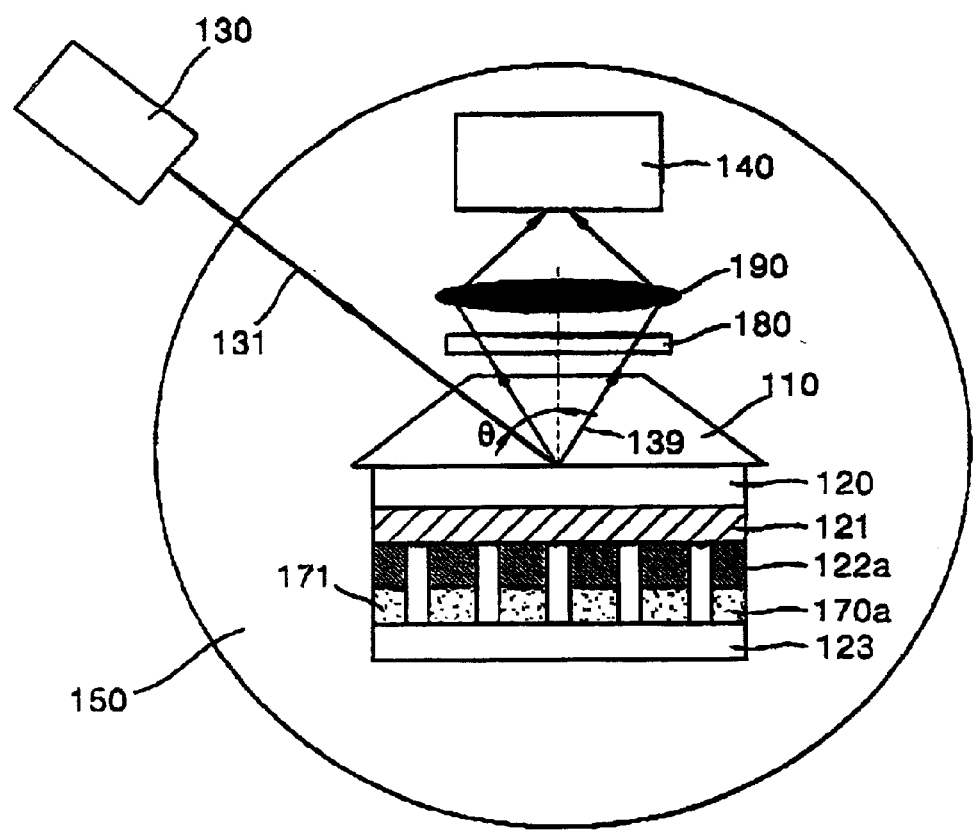
FIG. 10 shows the structure of a preferred embodiment of an AID WPR imaging system according to the present invention.

FIG. 10 shows the structure of a preferred embodiment of an AID WPR imaging system according to the present invention. The AID WPR imaging system of FIG. 10 has a similar structure to the AID WPR sensor, but includes conductive film arrays 122a and dielectric film arrays 170a as a grid pattern. The AID WPR imaging system images the sample 123 disposed closest to the conductive film arrays 122a based on surface plasmon resonance. The principle of the AID WPR imaging system is the same as the AID WPR sensor and thus a detailed description of the principle will not be provided here. The AID WPR imaging system uses a charge coupled device (CCD) or a photosensitive sheet as the photodetector 140 and images the sample 123 by detecting fluorescence intensities of the active ions 172 from each conductive film array 122a. The sample 123 is imaged with the contrast based on fluorescence intensity variations between each conductive film array 122a.

In the preferred embodiment of the AID WPR imaging system according to the present invention, the incident light beam 131 is incident onto the conductive thin array 122a through the dielectric medium 110, the index matching oil layer 120, and the glass substrate 121 at a particular incident angle θ at which CPWR occurs and then coupled to propagate into the dielectric film array 170a, thereby exciting the active ions 171 embedded in the dielectric film array 170a. Then, the intensity of the light 139 from the active ions 171 is measured. The intensity of the light 139 varies depending on the amount of the sample 123 attached to the dielectric film array 170a, i.e., topology of the sample 123. Therefore, topology of the sample 123 can be analyzed from fluorescent intensity variations and the sample 123 can be imaged with the contrast based on the fluorescent intensity variations.

According to the present invention, upconversion of the active ions 171 excited by the incident light beam 131 is coupled to surface plasmon resonance so that the light 139 of a shorter wavelength of the incident light beam 131 is emitted. The fluorescence intensity of the active ions 171 greatly varies according to changes in the incident angle of the incident light beam 131 in the imaging system according to the present invention and thus image data of the sample can be obtained with sensitivity 10–100 times greater than the conventional SPR sensor based imaging system.

As is apparent from the embodiments described above, an AID WPR sensor and an imaging system using the same according to the present invention include an additional dielectric thin film doped with active ions and acting as a waveguide on a metal thin film and measure the intensity of fluorescence induced by upconversion of the active ions coupled to surface plasmon resonance at an appropriate incident angle of light. The AID WPR sensor and the imaging system according to the present invention can detect a minor refractive index variation of $10^{-8}$, which could not be measured using a conventional SPR sensor, with 100 times larger refractive index resolution than the conventional SPR sensor. The AID WPR sensor and the imaging system according to the present invention can be applied to analyse molecules adsorbed onto a surface or a trace biological sample, without suffering the analytical limitations of the conventional SPR sensor, thereby leading to technical improvements in the biology and life science and engineering fields.

While this invention has been particularly shown and described with reference to preferred embodiments thereof, it will be understood by those skilled in the art that various changes in form and details may be made therein without departing from the spirit and scope of the invention as defined by the appended claims.

What is claimed is:

1. An active ion-doped waveguide-plasmon resonance (AID) WPR) sensor for analyzing a sample placed adjacent to a conductive thin film, comprising a conductive thin film for providing surface plasmons;

a dielectric medium disposed at one side of the conductive thin film;

a light source for emitting an incident light beam to the conductive thin film through the dielectric medium;

a dielectric thin film doped with active ions capable of fluorescing by being excited with the incident light beam, the dielectric thin film deposited at the surface of the conductive thin film opposite to the dielectric medium to act as an waveguide of surface plasmon waves and having a surface on which a sample is immobilized; and a photodetector for receiving and determining the intensity of fluorescence from the active ions.

2. The active ion-doped waveguide-plasmon resonance sensor of claim 1, wherein the photodetector determines a change in refractive index of the sample from the intensity of fluorescence to quantify and qualify the sample or to determine the thickness of the sample.

3. The active ion-doped waveguide-plasmon resonance sensor of claim 1, wherein the light source emits a transverse magnetic (TM) polarized light or transverse electric (TE) polarized light as the incident light beam.

4. The active ion-doped waveguide-plasmon resonance sensor of claim 1, wherein the light source emits a laser beam as the incident light beam.

5. The active ion-doped waveguide-plasmon resonance sensor of claim 1, wherein the conductive thin film is formed of one material selected from the group consisting of Au, Ag, Cu, Si, and Ge.

6. The active ion-doped waveguide-plasmon resonance sensor of claim 5, wherein the conductive thin film has a thickness of 35–50 nm.

7. The active ion-doped waveguide-plasmon resonance sensor of claim 1 wherein the conductive thin film is deposited on a bottom surface of a glass substrate, and the dielectric medium is disposed on top of the glass substrate.

8. The active ion-doped waveguide-plasmon resonance sensor of claim 7, further comprising a Cr layer or Ti layer to increase adhesion between the conductive thin film and the glass substrate.

9. The active ion-doped waveguide-plasmon resonance sensor of claim 7, further comprising an index matching oil layer between the glass substrate and the dielectric medium.

10. The active ion-doped waveguide-plasmon resonance sensor of claim 1, wherein the photodetector is one selected from the group consisting of photodiode, photomultiplier, charge coupled device, and photosensitive sheet.

11. The active ion-doped waveguide-plasmon resonance sensor of claim 1, wherein the dielectric medium is a trapezoidal prism.

12. The active ion-doped waveguide-plasmon resonance sensor of claim 1, further comprising an optical filter to increase the purity of the fluorescence from the active ions and received by the photodetector.

13. The active ion-doped waveguide-plasmon resonance sensor of claim 1, further comprising a lens for condensing the fluorescence from the active ions toward the photodetector.

14. The active ion-doped waveguide-plasmon resonance sensor of claim 1, wherein the incident light beam is incident onto the conductive thin film at a fixed incident angle.

15. The active ion-doped waveguide-plasmon resonance sensor of claim 1, wherein the dielectric thin film is formed of a layer selected from the group consisting of $SiO_2$ layer, $Al_2O_3$ layer, $TiO_2$ layer, $Ta_2O_3$ layer, $MgF_2$ layer, $Y_2O_3$ layer, $TeO_2$ layer, PbO layer, $LaF_3$ layer, ZnS layer, ZnSe layer, $Si_3N_4$ layer, AlN layer, or a composite layer of these layers.

16. The active ion-doped waveguide-plasmon resonance sensor of claim 1, wherein the active ions are derived from one selected from the group consisting of transition metal, rare-earth element, and organic dye.

17. The active ion-doped waveguide-plasmon resonance sensor of claim 16, wherein the active ions have the ability to fluoresce by emitting light of a shorter wavelength than the incident light beam through two-photon or three-photon absorption.

18. The active ion-doped waveguide-plasmon resonance sensor of claim 1, wherein the active ions are selected from the group consisting of $Tm^{3+}$ ions, $Er^{3+}$ ions, $Y^{3+}$ ions, $Ho^{3+}$—$Yb^{3+}$ composite ions, $Tm^{3+}$—$Yb^{3+}$ composite ions, $Er^{3+}$—$Yb^{3+}$ composite ions, and $Tm^{3+}$—$Nd^{3+}$ composite ions.

19. The active ion-doped waveguide-plasmon resonance sensor of claim 1, wherein the active ions are $Tm^{3+}$ ions and fluoresce light of a 350-nm wavelength by excitation with the incident light beam of a 650-nm wavelength.

20. The active ion-doped wavelength-plasmon resonance sensor of claim 1, wherein the active ions are , $Er^{3+}$ ions and fluoresce light of a 550-nm wavelength by excitation with the incident light beam of a 800-nm wavelength.

21. The active ion-doped wavelength-plasmon resonance sensor of claim 1, wherein the active ions are $Yb^{3+}$ ions and fluoresce light of a 480-nm wavelength by excitation with the incident light beam of a 980-nm wavelength.

22. The active ion-doped wave length-plasmon resonance sensor of claim 1, wherein the active ions are $Ho^{3+}$—$Yb^{3+}$ composite ions and fluoresce light of a 550-mn wavelength by excitation with the incident light beam of a 980-nm wavelength.

23. The active ion-doped wavelength-plasmon resonance sensor of claim 1, wherein the active ions are $Tm^{3+}$—$Yb^{3+}$ composite ions and fluoresce light of a 480-nm wavelength by excitation with the incident light beam of a 980-nm wavelength.

24. The active ion-doped wave length-plasmon resonance sensor of claim 1, wherein the active ions are $Er^{3+}$—$Yb^{3+}$ composite ions and fluoresce light of a 550-nm wavelength by excitation with the incident light beam of a 980-nm wavelength.

25. The active ion-doped wave length-plasmon resonance sensor of claim 1 wherein the active ions are $Tm^{3+}$—$Nd^{3+}$ composite ions and fluoresce light of a 480-nm wavelength by excitation with the incident light beam of a 800-nm wavelength.

26. The active ion-doped wavelength-plasmon resonance sensor at claim 1, wherein the dielectric thin film is thick enough to produce a coupled plasmon-waveguide resonance mode and attenuated total reflection leaky mode coupled to surface plasma resonance.

27. The active ion-doped wave length-plasmon resonance sensor of claim 1, wherein the dielectric thin film has a thickness of 100–700 mm.

28. The active ion-doped wavelength-plasmon resonance sensor of claim 1 wherein the sample is liquid, and the active ion-doped wavelength-plasmon resonance sensor further comprises a sample holder and a pump for sample circulating.

29. An active ion-doped wavelength-plasmon resonance imaging system for imaging a sample placed adjacent to a conductive thin film, the imaging system comprising:
  conductive film arrays for providing surface plasmons;
  a dielectric medium disposed at one side of the conductive film arrays;
  a light source for emitting an incident light beam to the conductive film arrays through the dielectric medium;
  dielectric film arrays doped with active ions capable of fluorescing by being excited with the incident light beam, the dielectric thin film deposited at the surface of the conductive film arrays opposite to the dielectric medium to act as an waveguide of surface plasmon waves and having a surface on which a sample is immobilized; and
  a photodetector for receiving the fluorescence from the active ions and imaging the sample from fluorescent intensity variations between each conductive film array.

30. The active ion-doped waveguide-plasmon resonance imaging system of claim 29, wherein the photodetector is one selected from the group consisting of photodiode, photomultiplier, charge coupled device, and photosensitive sheet.

31. The active ion-doped waveguide-plasmon resonance imaging system of claim 29, wherein the light source emits a transverse magnetic (TM) polarized light or transverse electric (TE) polarized light as the incident light beam.

32. The active ion-doped waveguide-plasmon resonance imaging system of claim 29, wherein the light source emits a laser beam as the incident light beam.

33. The active ion-doped waveguide-plasmon resonance imaging system of claim 29, wherein the conductive thin film is formed of one material selected from the group consisting of Au, Ag, Cu, Si, and Ge.

34. The active ion-doped waveguide-plasmon resonance imaging system of claim 33, wherein the conductive film arrays have a thickness of 35–50 nm.

35. The active ion-doped waveguide-plasmon resonance imaging system of claim 29, wherein the conductive film arrays are deposited on a bottom surface of the glass substrate, and the dielectric medium is disposed on top of the glass substrate.

36. The active ion-doped waveguide-plasmon resonance imaging system of claim 35, further comprising a Cr layer or Ti layer to increase adhesion between the conductive film arrays and the glass substrate.

37. The active ion-doped waveguide-plasmon resonance imaging system of claim 35, further comprising an index matching oil layer between the glass substrate and the dielectric medium.

38. The active ion-doped waveguide-plasmon resonance imaging system of claim 29, wherein the dielectric medium is a trapezoidal prism.

39. The active ion-doped waveguide-plasmon resonance imaging system of claim 29, further comprising an optical filter to increase the purity of the fluorescence from the active ions and received by the photodetector.

40. The active ion-doped waveguide-plasmon resonance imaging system of claim 29, further comprising a lens for condensing the fluorescence from the active ions toward the photodetector.

41. The active ion-doped waveguide-plasmon resonance imaging system of claim 29, wherein the incident light beam is incident onto the conductive film arrays at a fixed incident angle.

42. The active ion-doped waveguide-plasmon resonance imaging system of claim 29, wherein the dielectric thin film is formed of a layer selected from the group consisting of $SiO_2$ layer, $Al_2O_3$ layer $TiO_2$ layer, $Ta_2O_5$ layer, $MgF_2$ layer, $Y_2O_3$ layer, $TeO_2$ layer, PbO layer, $LaF_3$ layer, ZnS layer, ZnSe layer, $Si_3N_6$ layer, AlN layer, or a composite layer of these layers.

43. The active ion-doped waveguide-plasmon resonance imaging system of claim 29, wherein the active ions are derived from one selected from the group consisting of transition metal, rare-earth element, and organic dye.

44. The active on-doped waveguide-plasmon resonance imaging system of claim 43, wherein the active ions have the ability to fluoresce by emitting light of a shorter wavelength than the incident light beam through two-photon or three-photon absorption.

45. The active ion-doped waveguide-plasmon resonance imaging system of claim 29, wherein the active ions are selected from the group consisting of $Tm^{3+}$ ions, $Er^{3+}$ ions, $Yb^{3+}$ ions, $HO^{3+}$—$Yb^{3+}$ composite ions, $Tm^{3+}$—$Yb^{3+}$ composite ions, $Er^{3+}$—$Yb^{3+}$ composite ions, and $Tm^{3+}$—$Nd^{3+}$ composite ions.

46. The active ion-doped waveguide-plasmon resonance imaging system of claim 29, wherein the active ions are $Tm^{3+}$ ions and fluoresce light of a 350-nm wavelength by excitation with the incident light beam of a 650-nm wavelength.

47. The active ion-doped wave length-plasmon resonance imaging system of claim 29, wherein the active ions are $Er^{3+}$ ions and fluoresce light of a 550-nm wavelength by excitation with the incident light beam of a 800-nm wavelength.

48. The active ion-doped wave length-plasmon resonance imaging system of claim 29, wherein the active ions are $Yb^{3+}$ ions and fluoresce light of a 480-rim wavelength by excitation with the incident light beam of a 980-nm wavelength.

49. The active ion-doped wavelength-plasmon resonance imaging system of claim 29, wherein the active ions are $Ho^{3+}$—$Yb^{3+}$ composite ions and fluoresce light of a 550-nm wavelength by excitation with the incident light beam of a 980-nm wavelength.

50. The active ion-doped wave length-plasmon resonance imaging system of claim 29, wherein the active ions are $Tm^{3+}$—$Yb^{3+}$ composite ions and fluoresce light of a 480-nm wavelength by excitation with the incident light beam of a 980-nm wavelength.

51. The active ion-doped wave length-plasmon resonance imaging system of claim 29, wherein the active ions are $Er^{3+}$—$Yb^{3+}$ composite ions and fluoresce light of a 550-nm wavelength by excitation with the incident light beam of a 980-nm wavelength.

52. The active ion-doped wavelength -plasmon resonance imaging system of claim 29, wherein the active ions are $Tm^{3+}$—$Nd^{3+}$ composite ions and fluoresce light of a 480-nm wavelength by excitation with the incident light beam of a 800-nm wavelength.

53. The active ion-doped wave length-plasmon resonance imaging system of claim 29, wherein the dielectric thin film is thick enough to produce a coupled plasmon-waveguide resonance mode and attenuated total reflection leaky mode coupled to surface plasma resonance.

54. The active ion-doped wave length-plasmon resonance imaging system of claim 29, wherein the dielectric thin film has a thickness of 100–700 nm.

55. The active ion-doped wave length-plasmon resonance imaging system of claim 29, wherein the sample is liquid, and the active ion-doped wave length-plasmon resonance imaging system further comprises a sample holder and a pump for sample circulating.

* * * * *